(12) United States Patent
Fujioka

(10) Patent No.: US 11,414,332 B2
(45) Date of Patent: Aug. 16, 2022

(54) MICROORGANISM PREPARATION FEEDING METHOD, MICROORGANISM PREPARATION AUTOMATIC FEEDING APPARATUS, AND WASTEWATER PROCESSING SYSTEM

(71) Applicant: NISSAN CHEMICAL CORPORATION, Tokyo (JP)

(72) Inventor: Masatake Fujioka, Nagoya (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 173 days.

(21) Appl. No.: 16/612,172

(22) PCT Filed: May 9, 2018

(86) PCT No.: PCT/JP2018/017951
§ 371 (c)(1),
(2) Date: Nov. 8, 2019

(87) PCT Pub. No.: WO2018/207825
PCT Pub. Date: Nov. 15, 2018

(65) Prior Publication Data
US 2021/0130207 A1    May 6, 2021

(30) Foreign Application Priority Data

May 9, 2017 (JP) .............................. JP2017-093364
May 9, 2018 (JP) .............................. JP2018-090506

(51) Int. Cl.
*C02F 3/34* (2006.01)
*C02F 3/00* (2006.01)
(Continued)

(52) U.S. Cl.
CPC .............. *C02F 3/343* (2013.01); *C02F 3/006* (2013.01); *C02F 3/20* (2013.01); *C02F 3/347* (2013.01);
(Continued)

(58) Field of Classification Search
CPC .. C02F 3/343; C02F 3/006; C02F 3/20; C02F 3/347; C02F 2101/12; C02F 2103/32;
(Continued)

(56) References Cited

U.S. PATENT DOCUMENTS 4,226,939 A * 10/1980 Wegner .................... C12N 1/32
435/247
7,011,969 B2 * 3/2006 Yoneda .................. C07K 14/32
435/252.31

(Continued)

FOREIGN PATENT DOCUMENTS

CN      1310691 A       8/2001
EP      1 151 967 A1    11/2001
(Continued)

OTHER PUBLICATIONS

Kato, JP2011025200A , Method and apparatus for treating water, Espacenet translation, https://worldwide.espacenet.com/patent/search/family/043634587/publication/JP2011025200A?q=pn%3DJP2011025200A (Year: 2000).*

(Continued)

*Primary Examiner* — Nam X Nguyen
*Assistant Examiner* — Ekandra S. Miller-Cruz
(74) *Attorney, Agent, or Firm* — Birch, Stewart, Kolasch & Birch, LLP

(57) ABSTRACT

The microorganism preparation feeding method of the invention employs an automatic microorganism preparation feeding apparatus which includes a cold storage apparatus
(Continued)

for refrigeration-storing a seed microorganism belonging to the aerobic microorganism group including at least one species of aerobic microorganisms capable of decomposing oil and fat contained in oil/fat-including wastewater and a growth tank for growing the seed microorganism so as to produce the microorganism preparation, wherein the seed microorganism belonging to the aerobic microorganism group is maintained in a live state by means of the cold storage apparatus, the seed microorganism is periodically grown by means of the growth tank so as to produce a predetermined microorganism preparation, and the produced predetermined microorganism preparation is fed to the oil/fat-including wastewater. The method includes refrigeration-storing, as the seed microorganism, a microorganism whose population density is $1\times10^7$ CFU/mL to $5\times10^9$ CFU/mL in the cold storage apparatus; growing, as a source material, the seed microorganism of a predetermined volume by means of the growth tank so as to produce the predetermined microorganism preparation whose volume is 50 to 500 times the predetermined volume of the seed microorganism and whose population density is $1\times10^7$ CFU/mL to $2\times10^{10}$ CFU/mL; and feeding the produced microorganism preparation to the oil/fat-including wastewater.

11 Claims, 3 Drawing Sheets

(51) Int. Cl.
*C02F 3/20* (2006.01)
*C12M 1/12* (2006.01)
*C12M 1/02* (2006.01)
*C12M 1/00* (2006.01)
*C12M 1/36* (2006.01)
*C12N 1/16* (2006.01)
*C12N 1/20* (2006.01)
*C02F 101/12* (2006.01)
*C02F 103/32* (2006.01)

(52) U.S. Cl.
CPC ............ *C12M 23/06* (2013.01); *C12M 27/00* (2013.01); *C12M 39/00* (2013.01); *C12M 41/48* (2013.01); *C12N 1/16* (2013.01); *C12N 1/20* (2013.01); *C02F 2101/12* (2013.01); *C02F 2103/32* (2013.01); *C02F 2305/06* (2013.01)

(58) Field of Classification Search
CPC .. C02F 2305/06; C02F 2203/004; C02F 3/02; C02F 3/348; C02F 1/20; C12M 23/06; C12M 27/00; C12M 39/00; C12M 41/48; C12M 45/22; C12N 1/16; C12N 1/20; C12N 1/205; C12N 1/165; C12R 2001/72; C12R 2001/645; C12R 2001/01; Y02W 10/10
USPC .......................................... 210/606, 610, 611
See application file for complete search history.

(56) References Cited

U.S. PATENT DOCUMENTS

| | | | |
|---|---|---|---|
| 2010/0193430 A1 | 8/2010 | Whiteman | |
| 2015/0024470 A1 | 1/2015 | Hori et al. | |
| 2016/0002598 A1* | 1/2016 | Centeno | C12M 35/00 435/303.1 |

FOREIGN PATENT DOCUMENTS

| | | | | |
|---|---|---|---|---|
| JP | 6-347183 A | | 12/1994 | |
| JP | 2000-84587 A | | 3/2000 | |
| JP | 2000317491 A | * | 11/2000 | ............... C02F 3/08 |
| JP | 2000-354484 A | | 12/2000 | |
| JP | 2004-216286 A | | 8/2004 | |
| JP | 2006-247566 A | | 9/2006 | |
| JP | 2008-253989 A | | 10/2008 | |
| JP | 2009-39709 A | | 2/2009 | |
| JP | 2010-214310 A | | 9/2010 | |
| JP | 2011-25200 A | | 2/2011 | |
| JP | 2011230083 A | * | 11/2011 | ............... B09B 3/00 |
| JP | 5470614 B2 | | 4/2014 | |
| JP | 5640211 B2 | | 12/2014 | |
| JP | 5685783 B2 | | 3/2015 | |
| KR | 101272267 B1 | * | 6/2013 | ............. C02F 11/02 |
| WO | WO 2014/117140 A1 | | 7/2014 | |

OTHER PUBLICATIONS

Momiyama, JP2000-84587, Automatic culturing type sewage cleaning device, Espacenet translation, https://worldwide.espacenet.com/patent/search/family/017279303/publication/JP2000084587A?q=pn%3DJP2000084587A (Year: 2011).*
International Search Report issued in PCT/JP2018/017951 (PCT/ISA/210), dated Jul. 3, 2018.
Written Opinion of the International Searching Authority issued in PCT/JP2018/017951 (PCT/ISA/237), dated Jul. 3, 2018.
Extended European Search Report dated Dec. 3, 2020, in European Patent Application No. 18798932.2.
Chinese Office Action and Search Report for Chinese Application No. 201880030835.8, dated Sep. 9, 2021.
European Office Action for European Application No. 18 798 932.2 dated Dec. 7, 2021.

* cited by examiner

MICROORGANISM PREPARATION FEEDING METHOD, MICROORGANISM PREPARATION AUTOMATIC FEEDING APPARATUS, AND WASTEWATER PROCESSING SYSTEM

TECHNICAL FIELD

The present invention relates to a method for feeding a microorganism preparation (hereinafter may be referred to as a "microorganism preparation feeding method"), to an automatic apparatus for feeding a microorganism preparation (hereinafter may be referred to as a "microorganism preparation automatic feeding apparatus"), and to a wastewater processing system.

BACKGROUND ART

Conventionally, wastewater processing apparatuses for the food service industry have employed a grease trap, which is a wastewater processing apparatus for removing, via solid-liquid separation, oil contained in kitchen wastewater of the food-service industry. Also, useful microorganisms have been added to food plant wastewater, which contains a large amount of oil/fat (determined as an n-hexane extraction substance) (hereinafter referred to as "oil/fat-including wastewater"). More specifically, in such wastewater processing apparatus, a microorganism that can decompose oil/fat, organic substances, etc. is fed to a control tank, an aeration tank, a catalytic oxidation tank, and other tanks, whereby oil/fat contained in the grease trap, oil/fat-including wastewater, and the like is efficiently and totally decomposed by the microorganism.

Among the aforementioned microorganisms for the oil/fat treatment, there has been reported *Burkholderia arboris* SL1B1 strain (Accession number: NITE BP-00724), which secretes lipase (i.e., an oil/fat-hydrolyzing enzyme) (see Patent Document 1). There has also been reported a technique of promoting decomposition of oil/fat by use of a microorganism preparation employing the above microorganism in combination with *Candida cylindracea* SL1B2 strain (Accession number: NITE BP-00714), which is an effective glycerol assimilating microorganism (see Patent Document 2).

Hydrolysis reaction of oil/fat is reversible. Thus, as decomposition of oil/fat proceeds, fatty acid and glycerol (i.e., hydrolysis products) accumulate, resulting in a decrease in oil/fat decomposition rate). As disclosed in Patent Document 2, glycerol (i.e., one hydrolysis product) is removed by an effective glycerol assimilating microorganism, to thereby promote decomposition of oil/fat. However, the amount of fatty acid is highly dominant with respect to that of glycerol in the fat/oil decomposition product. The released fatty acid (free fatty acid) is an oil component and must also be removed, similar to the case of oil/fat. Particularly when a microorganism exhibiting considerably high oil/fat decomposition performance, such as the microorganism reported in Patent Document 1, is used, consumption of fatty acid by the microorganism cannot overcome formation of fatty acid. As a result, a large amount of free fatty acid accumulates in the treatment tank, thereby possibly causing a decrease in oil/fat decomposition efficiency.

The present inventor previously reported a technique of promoting decomposition of oil/fat by use of a microorganism preparation containing, in addition to the microorganisms disclosed in Patent Documents 1 and 2, *Yarrowia lipolytica* 1A1 strain (Accession number: NITE BP-1167) as a novel microorganism useful for decomposition of oil/fat and belonging to the genus *Yarrowia* microorganism (see Patent Document 3).

PRIOR ART DOCUMENTS

Patent Documents

Patent Document 1: Japanese Patent No. 5470614
Patent Document 2: Japanese Patent No. 5640211
Patent Document 3: Japanese Patent No. 5685783

SUMMARY OF THE INVENTION

Problem to be Solved by the Invention

According to the technique disclosed in Patent Document 3, oil/fat contained in oil/fat-including wastewater, a grease trap, etc. (i.e., process target) is decomposed by use of a microorganism preparation containing microorganisms belonging to two or more of the genuses *Yarrowia*, *Burkholderia*, and *Candida*. However, required amounts of microorganism preparations must be fed at specific intervals. As a result, a large amount of a microorganism preparation suited for each target is required, and heavy load is imposed on provision and feed of the microorganism preparation. Thus, there is demand for automatization of production and feed operation of microorganism preparations.

The present invention has been conceived in view of the foregoing. Thus, an object of the invention is to provide a microorganism preparation feeding method which can realize automation of production and feed of the microorganism preparation, a microorganism preparation automatic feeding apparatus, and a wastewater processing system.

Means for Solving the Problem

In a first mode of the present invention to attain the aforementioned object, there is provided a microorganism preparation feeding method characterized by use of an automatic microorganism preparation feeding apparatus which includes a cold storage apparatus for refrigeration-storing (i.e., storing under refrigeration) a seed microorganism belonging to the aerobic microorganism group including at least one species of aerobic microorganism capable of decomposing oil and fat contained in oil/fat-including wastewater and a growth tank for growing the seed microorganism so as to produce the microorganism preparation, wherein the seed microorganism belonging to the aerobic microorganism group is maintained in a live state by means of the cold storage apparatus, the seed microorganism is periodically grown by means of the growth tank so as to produce a predetermined microorganism preparation, and the produced predetermined microorganism preparation is fed to the oil/fat-including wastewater, the method comprising:

refrigeration-storing, as the seed microorganism, a microorganism whose population density is $1 \times 10^7$ CFU/mL to $5 \times 10^9$ CFU/mL in the cold storage apparatus;

growing, as a source material, the seed microorganism of a predetermined volume by means of the growth tank so as to produce the predetermined microorganism preparation whose volume is 50 to 500 times the predetermined volume of the seed microorganism and whose population density is $1 \times 10^7$ CFU/mL to $2 \times 10^{10}$ CFU/mL; and feeding the produced microorganism preparation to the oil/fat-including wastewater.

A second mode of the present invention is directed to a specific embodiment of the microorganism preparation feeding method of the first mode, wherein the growth of the seed microorganism in the growth tank is performed by use of the seed microorganism of the predetermined volume, water, an activating agent for activating the seed microorganism, and a carbon source composed of vegetable oil and growing the seed microorganism, and agitating them while introducing air into the growth tank.

A third mode of the present invention is directed to a specific embodiment of the microorganism preparation feeding method of the second mode, wherein the activating agent contains nitrogen, phosphorus, and potassium.

A fourth mode of the present invention is directed to a specific embodiment of the microorganism preparation feeding method of any of the first to third modes, wherein the growth of the seed microorganism is repeatedly performed every day such that the seed microorganism is grown once every 24 hours.

A fifth mode of the present invention is directed to a specific embodiment of the microorganism preparation feeding method of any of the first to third modes, wherein the method comprises:

a cleaning step of cleaning the growth tank at a first timing;

a water storage step of storing water of a predetermined amount in the growth tank at a second timing;

a growing step of supplying at a third timing to the growth tank the seed microorganism of the predetermined volume, an activating agent for activating the seed microorganism, and a carbon source composed of vegetable oil and growing the seed microorganism in respective predetermined amounts, and growing the seed microorganism to have a population density in a predetermined range by introducing air into a resultant mixture simultaneously with agitating and mixing the mixture in a state in which the mixture is maintained at a constant temperature; and a feeding step of feeding the microorganism preparation produced in the growing step to the oil/fat-including wastewater in a predetermined amount at a fourth timing.

A sixth mode of the present invention is directed to a specific embodiment of the microorganism preparation feeding method of the fifth mode, wherein the cleaning step, the water storage step, the growing step, and the feeding step are repeatedly performed every day such that each of the steps is performed once every 24 hours.

A seventh mode of the present invention is directed to a specific embodiment of the microorganism preparation feeding method of the fifth mode, wherein each of the cleaning step, the water storage step, the growing step, and the feeding step is repeatedly performed at intervals of 48 hours in each of two growth tanks such that each step is performed once every 48 hours and a time shift of 24 hours is present between each of the steps performed in one growth tank and the corresponding one of the steps performed in the other growth tank, whereby the microorganism preparation is fed to the oil/fat-including wastewater from the two growth tanks every day.

An eighth mode of the present invention is directed to a specific embodiment of the microorganism preparation feeding method of any of the fifth to seventh modes, wherein the method further comprises a dechlorination step of performing aeration for a predetermined period of time after tap water has been supplied to and stored in the growth tank, thereby removing chlorine from the tap water.

A ninth mode of the present invention is directed to a specific embodiment of the microorganism preparation feeding method of any of the first to eighth modes, which method further comprises a storing step of performing aeration at least once every 24 hours, by introducing air into a lower region of a cold storage of the cold storage apparatus which maintains the seed microorganism in a refrigerated state, so that convection of the contents of the cold storage is generated so as to introduce air into the contents, simultaneously with which to agitate and mix the contents, thereby maintaining the seed microorganism in a live state.

A tenth mode of the present invention is directed to a specific embodiment of the microorganism preparation feeding method of any of the first to ninth modes, wherein the aerobic microorganism group includes *Yarrowia lipolytica* 1A1 strain NITE BP-1167 and *Burkholderia arboris* SL1B1 strain NITE BP-00724.

An eleventh mode of the present invention is directed to a specific embodiment of the microorganism preparation feeding method of the tenth mode, wherein the aerobic microorganism group includes *Candida cylindracea* SL1B2 strain NITE BP-00714.

In a twelfth mode of the present invention to attain the aforementioned object, there is provided a microorganism preparation automatic feeding apparatus characterized by comprising:

cold storage means for refrigeration-storing a seed microorganism belonging to the aerobic microorganism group in a live state, the aerobic microorganism group including at least one species of aerobic microorganism capable of decomposing oil and fat contained in oil/fat-including wastewater;

first storage means for storing an activating agent for activating the seed microorganism;

second storage means for storing a carbon source composed of vegetable oil and growing the seed microorganism;

a growth tank for growing the seed microorganism so as to produce a microorganism preparation;

water supply means for supplying water to the growth tank;

agitating and mixing means for agitating and mixing contents of the growth tank;

feeding means for feeding the microorganism preparation produced in the growth tank to the oil/fat-including wastewater; and control means, wherein a microorganism whose population density is $1\times10^7$ CFU/mL to $5\times10^9$ CFU/mL is used as the seed microorganism, and wherein the control means repeatedly performs, at predetermined intervals, steps of supplying water into the growth tank by using the water supply means;

supplying the seed microorganism of the predetermined volume, the activating agent, and the carbon source to the growth tank;

agitating and mixing the contents of the growth tank by using the agitating and mixing means so as to grow the seed microorganism to have a population density within a predetermined range, thereby producing the microorganism preparation whose volume is 50 to 500 times the predetermined volume of the seed microorganism and whose population density is $1\times10^7$ CFU/mL to $2\times10^{10}$ CFU/mL; and feeding the produced microorganism preparation to the oil/fat-including wastewater by using the feeding means.

A thirteenth mode of the present invention is directed to a specific embodiment of the microorganism preparation automatic feeding apparatus of the twelfth mode, wherein the control means comprises:

a cleaning control section which controls a cleaning step of cleaning the growth tank at a first timing;

a water storage control section which controls a water storage step of storing water of a predetermined amount in the growth tank by the water supply means at a second timing;

a growth control section which controls a growing step of supplying at a third timing to the growth tank the seed microorganism, the activating agent, and the carbon source in respective predetermined amounts, and growing the seed microorganism to have a population density in a predetermined range, while performing agitation and mixing by the agitating and mixing means; and a feed control section which controls a feeding step of feeding the microorganism preparation to the oil/fat-including wastewater at a fourth timing by the feeding means.

A fourteenth mode of the present invention is directed to a specific embodiment of the microorganism preparation automatic feeding apparatus of the thirteenth mode, wherein the control means repeatedly performs the cleaning step, the water storage step, the growing step, and the feeding step every day such that each of the steps is performed once every 24 hours.

A fifteenth mode of the present invention is directed to a specific embodiment of the microorganism preparation automatic feeding apparatus of the thirteenth mode, wherein the apparatus has two growth tanks, and the control means repeatedly performs each of the cleaning step, the water storage step, the growing step, and the feeding step at intervals of 48 hours in each of the two growth tanks such that each step is performed once every 48 hours and a time shift of 24 hours is present between each of the steps performed in one growth tank and the corresponding one of the steps performed in the other growth tank, whereby the microorganism preparation is fed to the oil/fat-including wastewater from the two growth tanks alternatingly every day.

A sixteenth mode of the present invention is directed to a specific embodiment of the microorganism preparation automatic feeding apparatus of any of the thirteenth to fifteenth modes, wherein the control means includes a dechlorination control section which controls a dechlorination step of performing aeration for a predetermined period of time after the water storage control section has supplied tap water to the growth tank and stored the water in the tank, thereby removing chlorine from the tap water.

In a seventeenth mode of the present invention to attain the aforementioned object, there is provided a wastewater processing system comprising a microorganism preparation automatic feeding apparatus as recited in any one of the twelfth to sixteenth modes.

Effect of the Invention

The present invention enables provision of a microorganism preparation feeding method which realizes automatic production and feeding of a microorganism preparation, an automatic microorganism preparation feeding apparatus, and a wastewater processing system.

Figure 1:
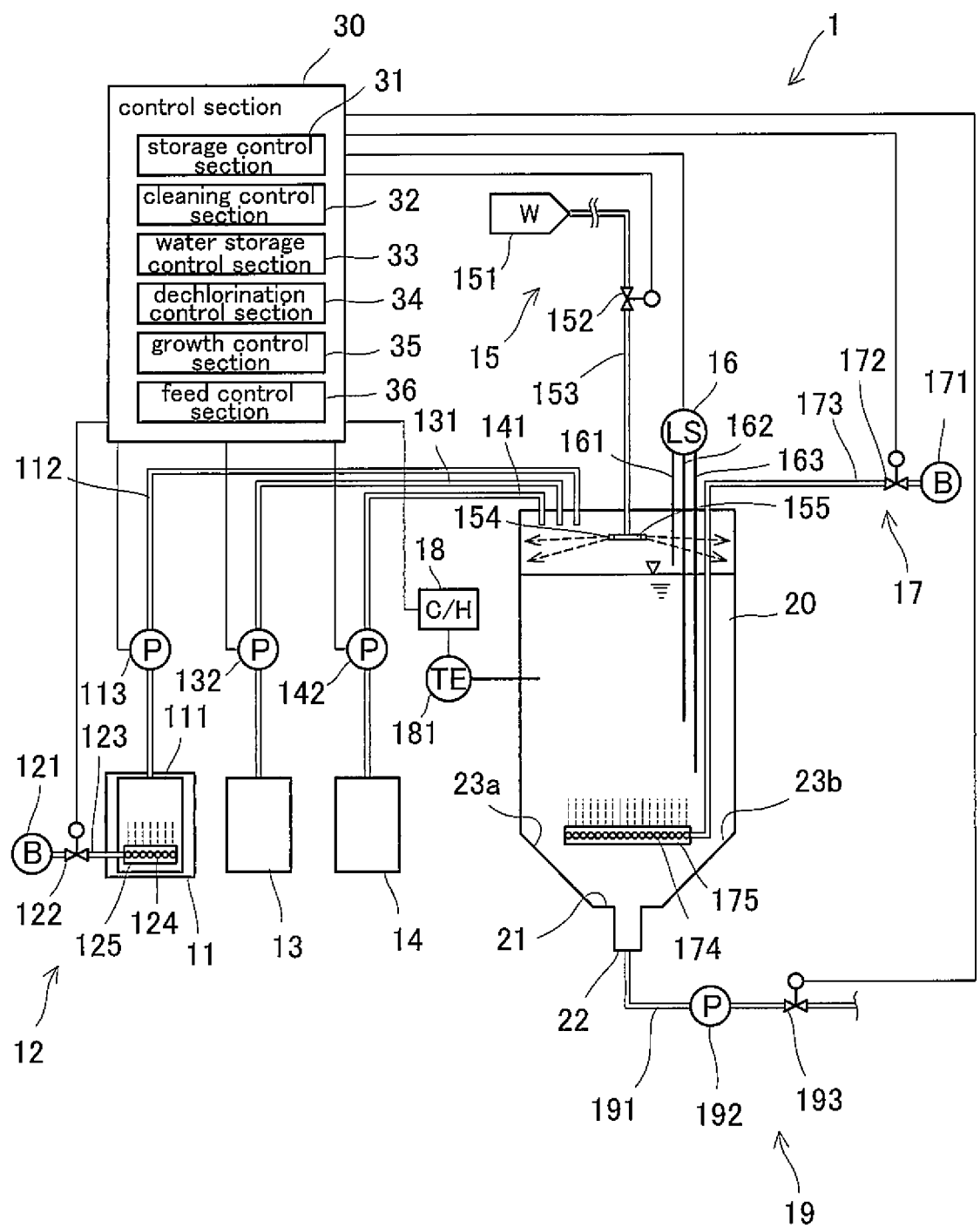
FIG. 1

An example of the configuration of the microorganism preparation automatic feeding apparatus according to an embodiment of the present invention.

FIG. 2

An example of the flow of feed of the microorganism preparation by means of the microorganism preparation automatic feeding apparatus according to the embodiment of the present invention.

FIG. 3

A block diagram showing an example of the structure of the wastewater processing system according to the embodiment of the present invention.

MODES FOR CARRYING OUT THE INVENTION (Microorganism Preparation Feeding Method)

The present invention employs an automatic apparatus for feeding a microorganism preparation (hereinafter may be referred to simply as "automatic feeding apparatus"), so as to realize periodically growth of a seed microorganism of a predetermined density which allows storage thereof, so as to multiply the population density by a predetermined factor; production of a target microorganism preparation having an increased seed microorganism population density and volume; and feeding of the microorganism preparation to oil/fat-including wastewater.

Conventionally, seed microorganisms are stored in a suspended animation state by attaching to a filler or the like. Generally, such a seed microorganism is activated before feeding to wastewater or the like upon use. However, according to the present invention, a seed microorganism is stored in a live state for a long period of time in an automatic feeding apparatus, where the microorganism is periodically grown. This is a completely new characteristic feature. The present invention has been accomplished on the basis of the following finding, which will next be described in detail.

Under such circumstances, the present inventor has first found that, when a specific seed microorganism of a predetermined population density is stored under specific conditions, the seed microorganism can be stored in a live state for a long period of time, and can be grown to an effective density within a short period of time upon use. The present invention has been accomplished on the basis of this finding.

Also, the inventor has found that, when a specific microorganism preparation is fed to a treatment target liquid such that the population density in the liquid falls within a predetermined range, oil/fat in the liquid can be effectively decomposed, regardless of the oil/fat amount in the treatment target liquid. This is another new characteristic feature of the invention. Specifically, the effective density in the treatment tank is, for example, $1\times10^5$ CFU/mL or higher, preferably $1\times10^6$ CFU/mL or higher. In the case where the capacity of the treatment tank is 100 m$^3$, a microorganism preparation having a population density of, for example, $1\times10^8$ CFU/mL or higher, preferably $1\times10^9$ CFU/mL or higher is fed in an amount of 100 L in total. For ensuring consistent wastewater treatment, feeding is preferably performed once a day. However, difficulty is encountered in providing a microorganism preparation in a volume of 100 L for every treatment procedure, and the apparatus which allows automatic feeding for a long period of time must have a considerably large scale. Furthermore, long-term storage of the microorganism preparation is difficult.

From the above viewpoints, the present invention employs a seed microorganism which can be stored in a live state for a long period of time. Specifically, a seed microorganism of a predetermined population density is used in a volume of, for example, $(1/500)\times100$ L to $(1/50)\times100$ L, and is grown every day, to thereby provide a microorganism preparation in a daily volume of 100 L for automatic feeding.

According to the present invention, a specific amount of a microorganism preparation of a specific population density can be provided in a relatively easy manner. Through feeding the thus-produced microorganism preparation to oil/fat-including wastewater, wastewater treatment can be performed at a grease trap, which is a wastewater processing apparatus for removing, via solid-liquid separation, oil contained in kitchen wastewater of the food-service industry, as well as to oil/fat-including wastewater such as food plant wastewater, which contains a large amount of oil/fat. As a result, the present invention attains the following excellent effects: prevention of malodor generation due to degrading of microorganisms, to thereby improve working environment, and simplification of the step of degrading microorganism.

As described above, no particular limitation is imposed on the configuration of the automatic feeding apparatus applicable to the present invention, so long as the apparatus allows storage of the seed microorganism and periodical growth of the seed microorganism, to thereby produce a target microorganism preparation, and feeding of the thus-produced microorganism preparation to oil/fat-including wastewater. For example, the below-described microorganism preparation automatic feeding apparatus 1 (see FIG. 1) may be employed.

As used herein, the specific (or predetermined) seed microorganism refers to a seed microorganism belonging to the aerobic microorganism group including at least one species of aerobic microorganism capable of decomposing oil and fat contained in oil/fat-including wastewater. The seed microorganism belonging to the aerobic microorganism group is a species belonging to the microorganism group including at least one aerobic microorganism capable of decomposing oil and fat contained in oil/fat-including wastewater. The aforementioned aerobic microorganism group preferably includes *Yarrowia lipolytica* 1A1 strain NITE BP-1167 and *Burkholderia arboris* SL1B1 strain NITE BP-00724), and may further include *Candida cylindracea* SL1B2 strain NITE BP-00714.

The seed microorganism density which allows storage thereof refers to a population density of a seed microorganism, which density allows storage of the microorganism for a period of interest under the below-mentioned conditions, and growth of the microorganism to such a population density as to provide a microorganism preparation. The seed microorganism which can be employed in the present invention has a population density of $1\times10^7$ CFU/mL to $5\times10^9$ CFU/mL. Through growth of the seed microorganism having such a population density, a predetermined microorganism preparation can be produced. That is, the thus-produced microorganism preparation has a volume 50 times to 500 times the volume of the seed microorganism and a population density of $1\times10^7$ CFU/mL to $2\times10^{10}$ CFU/mL. Storage of the seed microorganism will be described separately below.

The population density of the seed microorganism and the microorganism preparation is represented by the number of colonies formed per unit volume. More specifically, a specific amount of a correctly diluted sample is placed on a medium and subjected to culturing under specific conditions (e.g., 30° C. for 1 to 2 days). The number of formed colonies is determined. In a specific case in which a $10^6$-fold diluted sample solution (0.1 mL) is placed on a medium to thereby form 20 colonies, the population density of the sample is calculated as: $(20/0.1)\times10^6=2\times10^8$ CFU/mL.

No particular limitation is imposed on the above medium, and any customary culture medium may be used. Examples of the medium include an agar medium obtained by sterilization of a specific solution by means of an autoclave (in saturated vapor, at 121° C. and 2 atm, for 15 to 20 min). The aforementioned specific solution contains peptone (10 g), meat extract (10 g) (alternatively, yeast extract (1 g to 5 g)), sodium chloride (3 g), and agar powder (15 g), dissolved in ion-exchange water (1 L).

During the aforementioned culturing process, culturing in an aseptic room and/or use of a limiting medium is preferred, in order to prevent contamination with and growth of saprophytic bacteria.

Growth of the seed microorganism may be carried out by use of a seed microorganism, water, an activating agent which can activate the seed microorganism, and a carbon source composed of a vegetable oil, which source allows growth of the seed microorganism, in respective volumes. Specifically, the seed microorganism, water, the activating agent, and the carbon source (hereinafter these ingredients may be collectively referred to as "preparation ingredients") are fed to a growth tank of the automatic feeding apparatus, and the contents are agitated while air is introduced to the contents of the growth tank (i.e., aeration).

The activating agent for activating the seed microorganism contains nitrogen, phosphorus, and potassium. If needed, the agent may further include a metal, serving as a component of the seed microorganism.

The carbon source composed of vegetable oil and growing the seed microorganism is an essential ingredient for the growth of the seed microorganism. The carbon source serves as an acclimation source for the seed microorganism with respect to fat and oil, whereby a microorganism preparation suitable for decomposition of fat and oil is yielded. The carbon source is formed of a vegetable oil, for preventing growth of saprophytic bacteria. In addition, the carbon source may be appropriately varied in accordance with the type of oil/fat to be treated in the below-described wastewater processing system 200 (see FIG. 3). The oil/fat is preferably a vegetable oil. Examples of the vegetable oil include cotton seed oil, rape seed oil, soybean oil, corn oil, olive oil, safflower oil, rice oil, sesame oil, palm oil, coconut oil, and peanut oil. When the treatment target contains a large amount of animal fat/oil, lard, beef tallow, milk fat, and the like may be used. If needed, one or a plurality of carbon sources may be used.

The growth tank of the automatic feeding apparatus is a tank of a predetermined size which can contain the preparation ingredients and in which the seed microorganism can be grown so as to produce the microorganism preparation. The size of the growth tank may be appropriately designed in accordance with the volume of the microorganism preparation to be produced, and no particular limitation is imposed on the size of the growth tank. Although no particular limitation is imposed on the shape of the growth tank, the growth tank preferably has a shape for facilitating agitation of the contents. An example of the growth tank having such a shape is a cylindrical or polygonal tubular growth tank whose entirety is elongated in the vertical direction and whose bottom portion has an inverted conical shape or a shape obtained by squeezing the bottom portion toward the center in two directions. Alternatively, a horizontally elongated growth tank may be used. The number of the growth tanks may be determined appropriately. A single growth tank may be disposed or a plurality of growth tanks may be disposed.

Aeration is performed for supplying air necessary for growth of the seed microorganism. Agitation is performed so as to bring the seed microorganism into contact with the activating agent and the carbon source by mixing the contents, thereby promoting the growth of the seed microorganism. The present invention imposes no particular limitation on the means for aeration and agitation, so long as the seed microorganism can be grown. For example, there may be used an agitating and mixing means (e.g., a blower) which generates convection of the above-mentioned contents so as to introduce air and agitate and mix the contents.

Alternatively, an air introducing means for mechanically performing aeration (e.g., an air feed pump) and an agitating means (e.g., an agitating and mixing apparatus having agitation blades) may be used in combination. In the case of the above-described growth tank elongated in the vertical direction and having a slope at the bottom portion, since the contents can be agitated and mixed through generation of convection by the aeration, the agitating means is unnecessary.

In the present invention, the seed microorganism can be preserved. For preservation of the seed microorganism, the automatic feeding apparatus includes a storage means which can maintain the seed microorganism for a predetermined period of time in a state in which the growth of the seed microorganism is stopped and the seed microorganism lives while preventing growth of saprophytic bacteria. A cold storage means for maintaining the seed microorganism cold (e.g., a cold storage or an ice pack) is used as the storage means. Notably, in the automatic feeding apparatus, the above-described means for performing aeration and agitation may be provided in the storage means in order to maintain, for a predetermined period of time, the state in which the seed microorganism is maintained in live.

The present invention allows production of the microorganism preparation within the growth tank of the automatic feeding apparatus and feeding of the produced microorganism preparation into the oil/fat-including wastewater. For such a purpose, the automatic feeding apparatus preferably includes a feeding means which can feed the microorganism preparation into the oil/fat-including wastewater. No particular limitation is imposed on the configuration of the feeding means, so long as the feeding means can feed the microorganism preparation into the oil/fat-including wastewater. For example, in addition to preparation ingredient feed opening for feeding the ingredients of the microorganism preparation, a microorganism preparation feed opening for feeding the produced microorganism preparation into the oil/fat-including wastewater may be provided as the feeding means. In the case where the microorganism preparation feed opening is not provided, for example, the preparation ingredient feed opening may be used as the microorganism preparation feed opening. In either case, a liquid feed means (e.g., liquid feed pump) may be provided at the microorganism preparation feed opening (or the preparation ingredient feed opening). Thus, the microorganism preparation can be fed to the oil/fat-including wastewater by using the liquid feed means.

(Microorganism Preparation Automatic Feeding Apparatus)

Next, an automatic feeding apparatus for the microorganism preparation (hereinafter may be referred to as the "microorganism preparation automatic feeding apparatus") which realizes the feed of the above-described microorganism preparation will be described. Notably, in the following embodiment, an automatic feeding apparatus which includes a single growth tank for production of the microorganism preparation will be described as an example.

The present invention employs a microorganism preparation which is designed to be fed, once a day and in a predetermined amount, to an oil and fat decomposing tank at a population density in a predetermined range so as to process oil/fat-including wastewater in the oil and fat decomposing tank. The present invention realizes an automatic feeding apparatus which can produce the microorganism preparation in a predetermined amount every day and feed the produced microorganism preparation to the oil and fat decomposing tank.

The automatic feeding apparatus of the present invention uses a seed microorganism whose volume is, for example, 1/500 to 1/50 the necessary volume of the microorganism preparation and grows the seed microorganism so as to produce a predetermined volume of the microorganism preparation every day. The automatic feeding apparatus of the present invention can perform a growth preparation step to a growing step and further perform a feeding step in a 24 hour cycle.

Also, in order to allow the growth of the seed microorganism and the feed of the microorganism preparation to be repeatedly performed every day without maintenance, the automatic feeding apparatus is configured to supply, within a period of at least one month, preferably, two to three months, the seed microorganism and an activating agent and a carbon source for growth of the seed microorganism. A cold storage which will be described later is needed to maintain such a seed microorganism for 2 to 3 months.

Further, a microorganism whose population density is $1 \times 10^7$ CFU/mL to $5 \times 10^9$ CFU/mL is used as the seed microorganism, and the microorganism preparation whose volume is 50 to 500 times the volume of the seed microorganism and whose population density is $1 \times 10^7$ CFU/mL to $2 \times 10^{10}$ CFU/mL is repeatedly produced every day. For such production, the contents of the growth tank must be agitated and mixed. Notably, in the present invention, from the viewpoint of maintenance free operation and ease of cleaning, it is preferred that the growth tank has no mechanical agitating and mixing apparatus.

In the present invention, it is important to prevent growth of saprophytic bacteria during growth of the seed microorganism, and oil/fat is used as a carbon source in order to prevent growth of saprophytic bacteria. Thus, it becomes possible to repeatedly grow the seed microorganism every day. Also, growing the seed microorganism without growing saprophytic bacteria is important to obtain, through acclimation, the microorganism preparation suitable for decomposition of oil and fat.

In the present embodiment, there will be described an apparatus which is configured in consideration of the above-described point and which can automate all the steps of producing the microorganism preparation suitable for decomposition of oil and fat and feeding the produced microorganism preparation into oil/fat-including wastewater.

FIG. 1 shows an example of the configuration of the microorganism preparation automatic feeding apparatus according to the embodiment of the present invention. As shown in the drawing, the automatic feeding apparatus 1 includes a seed microorganism cold storage apparatus 11, a cold storage diffuser 12, an activating agent storage 13, a carbon source storage 14, a water supply apparatus 15, a water level monitoring apparatus 16, a growth tank diffuser 17, a temperature control apparatus 18, a feeding apparatus 19, a growth tank 20, and a control section 30. Notably, the automatic feeding apparatus 1 may include other components, if necessary.

The seed microorganism cold storage apparatus 11 is a cold storage means for refrigeration-storing a seed microorganism belonging to the aerobic microorganism group in a live state, the aerobic microorganism group including at least one species of aerobic microorganism capable of decomposing oil and fat contained in oil/fat-including wastewater. A cold storage 111 for refrigeration-storing the seed microorganism in a live state is provided in the seed microorganism cold storage apparatus 11. The seed microorganism in the cold storage 111 is supplied by a pump 113 to the growth tank 20 through a pipe 112. The cold storage diffuser 12 performs aeration in the cold storage 111 of the seed microorganism cold storage apparatus 11. Specifically, the cold storage diffuser 12 supplies air from a blower 121 to the cold storage 111 through a pipe 123 with a valve 122. An air discharge portion 125 having a plurality of air discharge openings 124 is attached an end of the pipe 123 on the cold storage 111 side and is disposed in a lower region of the cold storage 111. In the cold storage diffuser 12, air is supplied from the blower 121 through the pipe 123 and is discharged from the plurality of air discharge openings 124. Thus, convection of the contents of the cold storage 111 is generated, whereby air is introduced (aeration), and the contents are agitated and mixed so as to maintain the seed microorganism in a live state.

A microorganism similar to the above-described seed microorganism may be used as the seed microorganism belonging to the aerobic microorganism group.

The activating agent storage 13 is a first storage means for storing an activating agent which activates the seed microorganism belonging to the aerobic microorganism group. The activating agent in the activating agent storage 13 is supplied by a pump 132 to the growth tank 20 through a pipe 131. The activating agent contains nitrogen, phosphorus, and potassium. If necessary, a metal serving as a component of the seed microorganism may be added to the activating agent.

The carbon source storage 14 is a second storage means for storing a carbon source composed of vegetable oil and growing the seed microorganism belonging to the aerobic microorganism group. The carbon source in the carbon source storage 14 is supplied by a pump 142 to the growth tank 20 through a pipe 141. The carbon source is essential for growth of the seed microorganism. Vegetable oil is used as a carbon source in order to produce a microorganism preparation suitable for decomposition of oil and fat through acclimation of the seed microorganism to oil and fat and prevent growth of saprophytic bacteria. The carbon source may be changed appropriately in accordance with the type of oil and fat to be processed by a wastewater processing system 200 (see FIG. 3) to be described later. The oil/fat is preferably a vegetable oil. Examples of the vegetable oil include cotton seed oil, rape seed oil, soybean oil, corn oil, olive oil, safflower oil, rice oil, sesame oil, palm oil, coconut oil, and peanut oil. When the treatment target contains a large amount of animal fat/oil, lard, beef tallow, milk fat, and the like may be used. If needed, one or a plurality of carbon sources may be used.

The water supply apparatus 15 is a water supply means for supplying water from a water source 151 to the growth tank 20 through a water supply pipe 153 with a valve 152. The water supply apparatus 15 also functions as an apparatus for cleaning the growth tank 20. A water discharge portion 155 having water discharge openings 154 is provided at an end of the water supply pipe 153 on the growth tank 20 side. The water discharge portion 155 is disposed on the upper side of a central region of the growth tank 20. In the present embodiment, the water discharge openings 154 are disposed in the water discharge portion 155 such that the water discharge openings 154 face the side wall of the growth tank 20 and water is discharged toward the side wall of the growth tank 20. Dirt in the growth tank 20, in particular, dirt adhering to the side wall of the growth tank 20, can be removed by the water discharged through from the water discharge openings 154. Removal of dirt prevents clogging of the growth tank 20 and prevents growth of saprophytic bacteria other than the oil/fat decomposing aerobic microorganism group. The structure of the water discharge portion 155 is not limited to the above-described structure. For example, the water discharge portion 155 may rotate about a vertical axis such that the water discharge openings 154 move in the circumferential direction. The water supplied to the growth tank 20 by the water supply apparatus 15 may be tap water (purified water), pure water, ion-exchanged water, or industrial water. No particular limitation is imposed on the water supplied to the growth tank 20 so long as the water does not inhibit the growth of the seed microorganism belonging to the aerobic microorganism group. Tap water is preferred because tap water does not inhibit the growth of the seed microorganism of the aerobic microorganism group, prevents the growth of saprophytic bacteria other than the oil/fat decomposing aerobic microorganism group, and is cost-effective.

The water level monitoring apparatus 16 is a level sensor (liquid level sensor) for monitoring the level of water supplied to the growth tank 20 by the water supply apparatus 15. No particular limitation is imposed on the structure of the water level monitoring apparatus 16. For example, the water level monitoring apparatus 16 is composed of an upper level sensor 161, an earth sensor 162, and a lower level sensor 163. The water level monitoring apparatus 16 monitors the water level of the growth tank 20 by means of the upper level sensor 161 and the earth sensor 162 and adjusts the opening and closing of the valve 152 of the water supply apparatus 15. The water level monitoring apparatus 16 detects completion of feed of the microorganism preparation by monitoring the water level of the growth tank 20 by means of the lower level sensor 163.

The growth tank diffuser 17 supplies air from a blower 171 to the growth tank 20 through a pipe 173 with a valve 172. An air discharge portion 175 having a plurality of air discharge openings 174 is provided at an end of the pipe 173 on the growth tank 20 side. The air discharge portion 175 is formed of a straight pipe member disposed to cross a lower region of the growth tank 20. The plurality of air discharge openings 174 are provided in opposite sides of the air discharge portion 175, which are located diagonally upward. Namely, the growth tank diffuser 17 is an agitating and mixing means for suppling air from the blower 171 through the pipe 173 and discharging the air from the plurality of air discharge openings 174 so as to introduce air into the contents of the growth tank 20 (aeration) and generate convection for agitating and mixing the contents, thereby bringing the activating agent and the carbon source into contact with the seed microorganism belonging to the aerobic microorganism group for the purpose of promoting the growth of the seed microorganism. The air discharge portion 175 having the plurality of air discharge openings 174 may be a pipe formed of, for example, resin (e.g., polyvinyl chloride) or metal (e.g., stainless steel) and having a plurality of holes having a diameter of, for example, about 1.5 cm formed on the periphery thereof as the air discharge openings 174. A material which reduces the likelihood of clogging caused by the carbon source (vegetable oil) is preferably used for the air discharge portion 175, and polyvinyl chloride is preferred. Notably, ceramic materials are not preferred because they increase the likelihood of clogging caused by the carbon source.

The temperature control apparatus 18 is a temperature control means for controlling the temperature inside the growth tank 20, and uses a thermocouple 181 as a temperature sensor. Specifically, the temperature control apparatus 18 includes a heater and a cooler for maintaining the temperature inside the growth tank 20 at a predetermined temperature.

The feeding apparatus 19 is a feeding means for feeding the microorganism preparation produced in the growth tank 20 into oil/fat-including wastewater. Through a feed pipe 191 of the feeding apparatus 19, a pump 192 and a valve 193 are connected to a feed opening 22 provided in a bottom wall 21 of the growth tank 20, which will be described later. In the feeding apparatus 19, the microorganism preparation in the growth tank 20 is fed by the pump 192 to the oil/fat-including wastewater through the feed pipe 191.

The growth tank 20 is preferably a cylindrical or polygonal tubular growth tank whose entirety is elongated in the vertical direction and whose bottom portion has an inverted conical shape or a shape obtained by squeezing the bottom portion toward the center in two directions. The feed opening 22 for feeding the microorganism preparation into the oil/fat-including wastewater is provided on the bottom wall 21 side of the growth tank 20 of the present embodiment. A side wall portion of the growth tank 20 located on the bottom wall 21 side has sloping surfaces 23a and 23b sloping toward the feed opening 22. In production of the microorganism preparation, the supplied seed microorganism belonging to the aerobic microorganism group, the supplied activating agent, and the supplied carbon source (hereinafter, collectively referred to as "preparation ingredients") may stagnate on the bottom wall 21 side of the growth tank 20. The aeration by the growth tank diffuser 17 causes the preparation ingredients to move upward toward the surface of water along the sloping surfaces 23a and 23b of the bottom wall 21 of the growth tank 20. As a result, the preparation ingredients repeat upward and downward movements in the growth tank 20, thereby generating convection. As a result, a mixture of the preparation ingredients is obtained in such a state in which the density distributions of the preparation ingredients within the growth tank 20 are maintained uniform without local increase in density on the bottom wall 21 side. Notably, in the present embodiment, since the vertically elongated growth tank 20 is used, the preparation ingredients can be agitated and mixed without use of an agitating and mixing apparatus. However, in the case where an agitating and mixing apparatus is used, no particular limitation is imposed on the shape of the growth tank, and, for example, a horizontally elongated growth tank may be used. If necessary, a plurality of growth tanks 20 may be disposed. For example, two growth tanks 20 may be disposed.

The control section 30 includes a storage control section 31 which controls a storing step of maintaining the seed microorganism belonging to the aerobic microorganism group in a live state; a cleaning control section 32 which controls a cleaning step of cleaning the growth tank 20; a water storage control section 33 which controls a water storage step of storing a predetermined amount of water in the growth tank 20 by means of the water supply apparatus 15; a dechlorination control section 34 which controls a dechlorination step of removing chlorine from the growth tank 20 by performing aeration for a predetermined period of time; a growth control section 35 which controls a growing step of growing the seed microorganism to have a population density within a predetermined range; and a feed control section 36 which controls a feeding step of feeding the microorganism preparation into the oil/fat-including wastewater. The control section 30 is a control means for controlling microorganism preparation production conditions (e.g., the amounts and timings of supply of the preparation ingredients and environment) and feed conditions (e.g., the amount and timing of supply of the produced microorganism preparation into the oil/fat-including wastewater).

The storage control section 31 performs aeration within the cold storage 111 by activating the blower 121 of the cold storage diffuser 12 and opening and closing the valve 122. At that time, the amount of introduced air is controlled by adjusting the opening and closing of the valve 122. Although not illustrated, the temperature inside the cold storage 111 of the seed microorganism cold storage apparatus 11 is controlled so as to maintain the seed microorganism in a refrigerated state. The maintaining temperature is low enough to lower the activity of the seed microorganism. The maintaining temperature is, for example, 0° C. to 20° C., and is preferably 0° C. to 10° C. In the present embodiment, the temperature inside the cold storage 111 is set to 4° C. so as to maintain the seed microorganism in a refrigerated state.

The cleaning control section 32 supplies water to the growth tank 20 by opening and closing the valve 152 of the water supply apparatus 15. At that time, the water is discharged from the water discharge openings 154 of the water discharge portion 155 toward the side wall of the growth tank 20, whereby dirt is removed from the side wall. The cleaning time of the growth tank 20 is appropriately determined in accordance with the size and shape of the growth tank 20 or the number of the growth tanks. For example, in the case of the vertically elongated growth tank 20 having a capacity of 100 L, the cleaning time is 10 min to 15 min. The cleaning control section 32 may open and close the valve 152 on the basis of time by means of a timer or the like. Alternatively, the cleaning control section 32 may control the valve 152 by means of, for example, a sensor for detecting dirt within the growth tank 20. Notably, wastewater produced as a result of cleaning is discharged from the feed opening 22 of the growth tank 20 and is processed, together with the oil/fat-including wastewater, etc., by the wastewater processing system 200 (see FIG. 3) which will be described later.

The water storage control section 33 supplies water to the growth tank 20 by opening and closing the valve 152 of the water supply apparatus 15, monitors the water level of the growth tank 20 by means of the upper level sensor 161 and the earth sensor 162 of the water level monitoring apparatus 16, and adjusts the opening and closing of the valve 152 of the water supply apparatus 15, thereby controlling the water supply amount. At that time, when water within the growth tank 20 is detected by the earth sensor 162 and the surface of water within the growth tank 20 is detected by the upper level sensor 161, the water storage control section 33 determines that a predetermined amount of water has been stored and ends the water supplying operation by closing the valve 152 of the water supply apparatus 15.

The dechlorination control section 34 performs aeration within the growth tank 20 by activating the blower 171 of the growth tank diffuser 17 and opening and closing the valve 172. At that time, the amount of introduced air is controlled by adjusting the opening and closing of the valve 172. Also, the dechlorination control section 34 controls the temperature inside the growth tank 20 by means of the thermocouple 181 of the temperature control apparatus 18, thereby maintaining a temperature suitable for performing a dechlorination treatment for water. The temperature of the dechlorination treatment is appropriately determined in accordance with the water supplied to the growth tank 20. For example, in the case where tap water is supplied, the temperature inside the growth tank 20 is preferably maintained at 20° C. to 40° C., more preferably, 25° C. to 35° C. The period of time of the dechlorination treatment is appropriately determined in accordance with the size and shape of the growth tank(s) 20 or the number of the growth tanks 20. For example, in the case of the vertically elongated growth tank 20 having a capacity of 100 L, a dechlorination treatment time of about 3 hours to 6 hours is sufficient.

The growth control section 35 supplies the seed microorganism belonging to the aerobic microorganism group in the cold storage 111 to the growth tank 20 by activating the pump 113 of the seed microorganism cold storage apparatus 11, supplies the activating agent to the growth tank 20 by activating the pump 132 of the activating agent storage 13, and supplies the carbon source to the growth tank 20 by activating the pump 142 of the carbon source storage 14. At that time, the growth control section 35 controls the supply amounts of the seed microorganism, the activating agent, and the carbon source by activating the pumps 113, 132, and 142, respectively. Also, the growth control section 35 performs aeration within the growth tank 20 by activating the blower 171 of the growth tank diffuser 17 and opening and closing the valve 172. At that time, the amount of introduced air is controlled by adjusting the opening and closing of the valve 172. Further, the growth control section 35 controls the temperature inside the growth tank 20 by means of the thermocouple 181 of the temperature control apparatus 18, thereby maintaining a temperature suitable for growth of the seed microorganism. The temperature and time of growth of the seed microorganism are appropriately determined in accordance with the seed microorganism supplied to the growth tank 20. For example, in the case where *Yarrowia lipolytica* 1A1 strain NITE BP-1167 and *Burkholderia arboris* SL1B1 strain NITE BP-00724 are supplied to the growth tank 20, the temperature inside the growth tank 20 is preferably maintained at 20° C. to 40° C. or 25° C. to 35° C., and the growth time is preferably set to 12 hours to 20 hours.

The feed control section 36 delivers the microorganism preparation in the growth tank 20 into the oil/fat-including wastewater (which will be described later) by activating the pump 192 of the feeding apparatus 19 and opening and closing the valve 193. At that time, the amount of the delivered microorganism preparation is controlled by adjusting the opening and closing of the valve 193. Further, the feed control section 36 monitors the water level within the growth tank 20 by means of the lower level sensor 163 of the water level monitoring apparatus 16. When the surface of water within the growth tank 20 is detected, the feed control section 36 ends the feed of the microorganism preparation by closing the valve 193.

In the present embodiment, a microorganism preparation feeding method using the microorganism preparation automatic feeding apparatus 1 will be described as an example on the basis of a microorganism preparation feeding flow. However, the steps (which will be described below) of the microorganism preparation feeding method are not limited thereto. In the present invention, the number of steps may be increased or decreased in accordance with an apparatus to be used so long as the microorganism preparation feeding method includes at least a cleaning step, a water storage step, a growing step, and a feeding step which will be described later.

Figure 2:
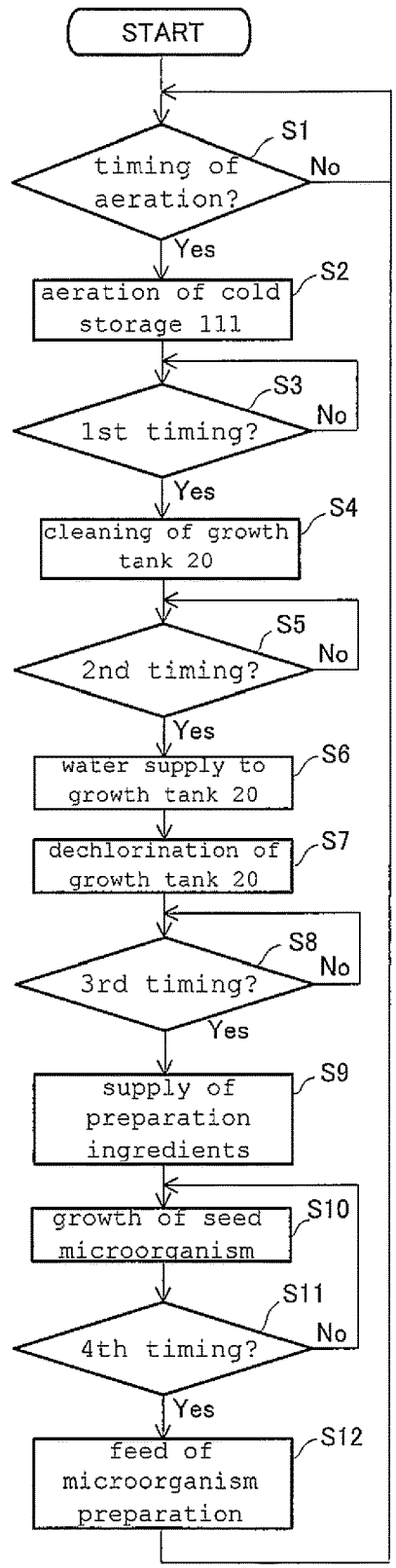

FIG. 2 shows an example of the flow of feed of the microorganism preparation by means of the microorganism preparation automatic feeding apparatus 1 (see FIG. 1) according to the embodiment of the present invention. As shown in FIG. 2, first, the storage control section 31 of the control section 30 determines whether or not a timing of performing aeration of the cold storage 111 has come (step S1). In the case where the timing of performing aeration has come (step S1; Yes), the aeration of the cold storage 111 is performed (step S2), and the flow proceeds to step S3. Meanwhile, in the case where the timing of performing aeration has not yet come (step S1; No), the above-determination is performed again (step S1).

In the storing step (step S1 to step S2), aeration of the cold storage 111 is performed at least once every 24 hours although no particular limitation is imposed on the timing at which aeration of the cold storage 111 is performed. In step S2, air is introduced into a lower region of the cold storage 111 which maintains the seed microorganism in a refrigerated state. As a result, convection of the contents of the cold storage 111 occurs, whereby aeration is performed; i.e., air is introduced into the contents and the contents are agitated and mixed. In this manner, the seed microorganism belonging to the aerobic microorganism group is maintained in a live state.

Next, the cleaning control section 32 determines whether or not a first timing of cleaning the growth tank 20 has come (step S3). In the case where the timing of cleaning the growth tank 20 has come (step S3; Yes), cleaning of the growth tank 20 is performed (step S4), and the flow proceeds to step S5. Meanwhile, in the case where the timing of cleaning the growth tank 20 has not yet come (step S3; No), the above-determination is performed again (step S3).

Next, the water storage control section 33 determines whether or not a second timing of supplying water to the growth tank 20 has come (step S5). In the case where the timing of supplying water has come (step S5; Yes), water is supplied to the growth tank 20 (step S6), and the flow proceeds to step S7. Meanwhile, in the case where the timing of supplying water has not yet come (step S5; No), the above-determination is performed again (step S5).

In step S6 of a water storage step (step S5 to step S6), for example, tap water is supplied through use of the water supply apparatus 15, because the stored water can have a pH of 6 to 7 which establishes an optimal growth environment without inhibiting the growth of the seed microorganism. Although not illustrated in the drawings, the water level of the growth tank 20 is monitored through use of the water level monitoring apparatus 16. When it is determined that a predetermined amount of water has been stored, the valve 152 of the water supply apparatus 15 is closed so as to complete the water storing operation.

After the completion of the water storing operation, the water storage control section 33 removes chlorine from the growth tank 20 by means of the dechlorination control section 34 (step S7). Subsequently, the flow proceeds to step S8.

In the dechlorination step (step S7), chlorine is removed from the growth tank 20. Although the time of aeration is appropriately determined in accordance with the required level of aeration, aeration is preferably performed, for example, three hours to six hours.

Next, the growth control section 35 determines whether or not a third timing has come (step S8). The third timing is a timing for supplying to the growth tank 20 the seed microorganism belonging to the aerobic microorganism group including at least one species of aerobic microorganism capable of decomposing oil and fat contained in the oil/fat-including wastewater, the activating agent for activating the seed microorganism, and the carbon source (vegetable oil) for growing the seed microorganism (hereinafter, these will be correctively referred to "preparation ingredients"). In the case where the timing of supplying the preparation ingredients has not yet come (step S8; No), the growth control section 35 waits. In the case where the timing of supplying the preparation ingredients has come (step S8; Yes), the growth control section 35 supplies the preparation ingredients (step S9) and continues the growth of the seed microorganism within the growth tank 20 (step S10).

In step S9 of the growing step (step S8 to step S10), the growth control section 35 supplies the preparation ingredients to the growth tank 20 in respective amounts. In step S10 of the growing step, the growth control section 35 performs aeration by introducing air into a lower region of the growth tank 20, while maintaining the temperature inside the growth tank 20 at a constant temperature. As a result, the seed microorganism is grown to have a population density within a predetermined range.

Notably, the population densities and volumes of the seed microorganism and the microorganism preparation may be similar to the above-described population densities and volumes of the seed microorganism and the microorganism preparation.

Next, the feed control section 36 determines whether or not a fourth timing of feeding the microorganism preparation has come (step S11). In the case where the feed timing has come (step S11; Yes), the feed control section 36 delivers the microorganism preparation (step S12). After that the flow returns to step S1. Meanwhile, in the case where the feed timing has not yet come (step S11; No); i.e., in the case where the seed microorganism has not yet grown to have a population density within the predetermined range, the flow returns to step S10.

Although no particularly limitation is imposed on the fourth timing of feeding the microorganism preparation, the feeding step (step S11 to step S12) is repeatedly performed every day (once every 24 hours) after the growing step. In step S12, the microorganism preparation produced in the growing step is fed to the oil/fat-including wastewater in a predetermined amount. No particular limitation is imposed on the feed amount of the microorganism preparation, and the feed amount of the microorganism preparation may be appropriately determined in accordance with the processing amount and time of the oil/fat-including wastewater.

In the above-described embodiment, the microorganism preparation automatic feeding apparatus 1 is programmed to perform each of the steps of cleaning the growth tank 20 (step S4), storing water in the growth tank 20 (step S6), removing chlorine from the growth tank 20 (step S7), supplying preparation ingredients into the growth tank 20 (step S9), growing the seed microorganism (step S10), and feeding the microorganism preparation (step S12) once every 24 hours such that all the steps are completed for 24 hours. When the time (timing) of feeding the microorganism preparation is determined, all the other timings are set to appropriate predetermined times.

In the above-described example, the aeration of the cold storage 111 is performed once every 24 hours. However, the aeration may be performed at any timing, so long as the timing of the aeration of the cold storage 111 differs from the timing of the feed of the microorganism preparation. For example, the aeration of the cold storage 111 may be performed immediately before the feed of the seed microorganism to the growth tank 20 (between step S8 and step S9) from the viewpoint of making the population of the seed microorganism supplied to the growth tank 20 uniform and feeding the seed microorganism into the growth tank 20 while maintaining that state.

In the above-described embodiment, each of the steps is performed once every 24 hours such that all the steps are completed for 24 hours. However, a larger feed amount of the microorganism preparation or a certain type of the seed microorganism requires a longer growth time, and in such a case, conceivably, the growth step does not end within 24 hours. For example, in the case where all the steps end within a period which is not shorter than 24 hours and not longer than 48 hours, two growth tanks 20 are disposed, and the above-described steps are performed for each growth tank 20 such that a time shift of 24 hours is preset between the steps for one growth tank 20 and the steps for the other growth tank 20. Namely, 48-hour repeated growth of the seed microorganism is performed alternatingly in the growth tanks 20, whereby the microorganism preparation can be fed to the oil/fat-including wastewater once every 24 hours.

(Wastewater Processing System)

Figure 3:
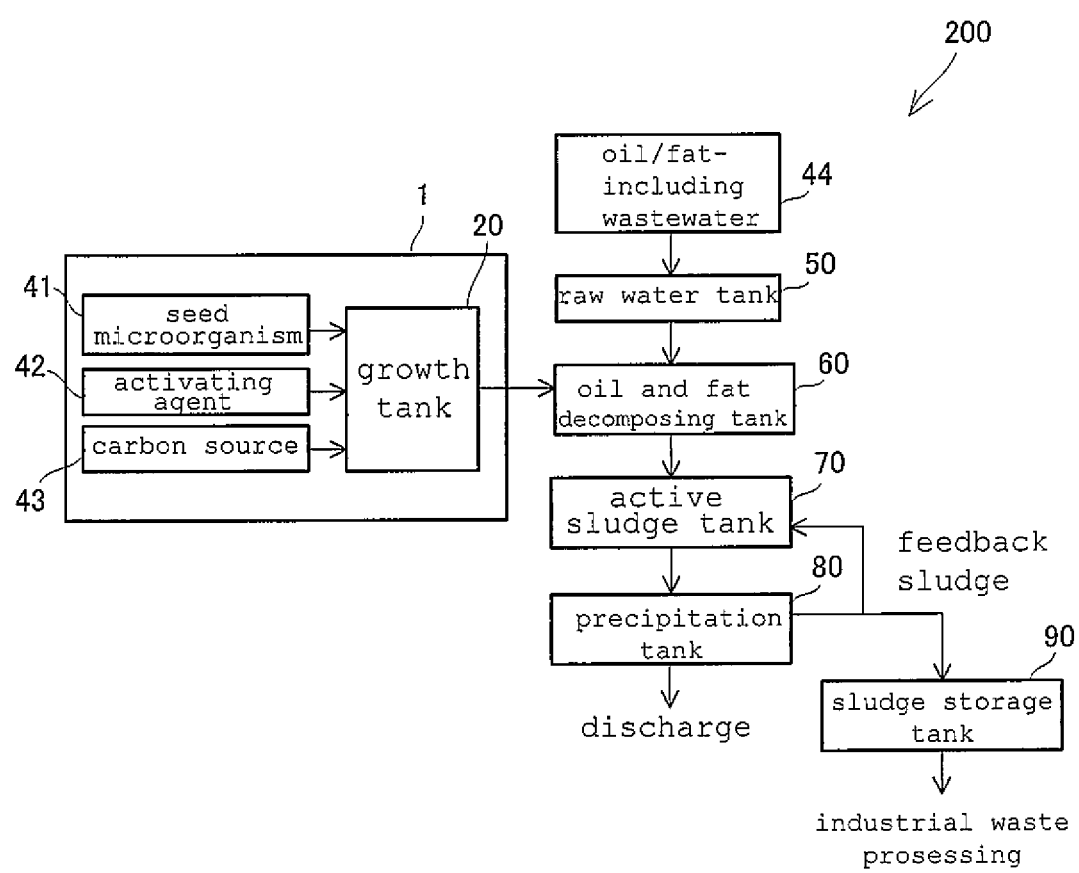

Next, a wastewater processing system to which the automatic feeding apparatus 1 is applied will be described. FIG. 3 is a block diagram showing an example of the structure of the wastewater processing system according to the embodiment of the present invention. As shown in FIG. 3, in the wastewater processing system 200, oil/fat-including wastewater 44 containing a large amount of oil and fat (e.g., wastewater from a food plant or a grease trap which is a processing facility of removing, through solid liquid separation, the oil component contained in wastewater from kitchens of the food service industry) is collected into a raw water tank 50. When the collected water reaches a predetermined level, the collected water is fed to an oil and fat decomposing tank 60. The microorganism preparation is fed to the oil and fat decomposing tank 60 by the automatic feeding apparatus 1. The microorganism preparation is obtained by supplying the seed microorganism 41, the activating agent 42, and the carbon source 43 to the growth tank 20 followed by growth and acclimation. In the oil and fat decomposing tank 60, the oil and fat contained in the oil/fat-including wastewater 44 are decomposed by the microorganism preparation, and the product is fed to an active sludge tank 70. In the active sludge tank 70, organic substances, etc. are decomposed by microorganisms, and the resultant product is fed to a precipitation tank 80. In the precipitation tank 80, the supernatant fluid above the precipitate is discharged, and the precipitate is returned to the active sludge tank 70 (return sludge). The precipitate remaining to the last in the precipitation tank 80 is collected into a sludge storage tank 90. When the collected precipitate in the sludge storage tank 90 reaches a predetermined level, the collected precipitate is disposed of as industrial waste. Notably, the above-described wastewater processing system 200 is a mere example. The wastewater processing system 200 may include other structural components, and any of the above-described structural components may be omitted.

OTHER EMBODIMENTS

The above-described automatic feeding apparatus of the present embodiment includes the growth tank diffuser which supplies air from a blower to the growth tank through a pipe with a valve. However, the structure of the automatic feeding apparatus is not limited to such a structure, so long as air can be introduced into the growth tank.

Instead of the growth tank diffuser, for example, an agitating means (e.g., an agitating and mixing apparatus having agitation blades) may be used. Use of such an agitating and mixing apparatus enables mechanical agitation of the contents of the growth tank for introduction of air. As a result, it is possible to introduce air into the tank while agitating and mixing the contents. Accordingly, in this case, only the agitating means is provided without use of an air introduction means such as a blower (air feed pump).

In the case where it is difficult to introduce air into the tank by the agitating means only, the air introduction means may be used together with the agitating means. Simultaneous use of these means makes it possible to reliably introduce air into the tank while agitating and mixing the contents.

In the case where the agitating and mixing apparatus is used, since it is unnecessary to generate convection, for example, a horizontally elongated growth tank may be used instead of the vertically elongated growth tank.

In the automatic feeding apparatus of the present embodiment, a cold storage is provided in the seed microorganism cold storage apparatus so as to maintain the seed microorganism in a live state. However, the structure of the automatic feeding apparatus is not limited to such a structure. Instead of the cold storage, a cold storage means such as an ice pack may be used.

The seed microorganism cold storage apparatus has the cold storage diffuser which can supply air from a blower to the cold storage through a pipe with a valve so as to produce convection within the tank, thereby agitating and mixing the contents. However, the structure of the automatic feeding apparatus is not limited to such a structure so long as air can be supplied to the cold storage. Instead of the cold storage diffuser, for example, the above-described agitating means may be provided or the agitating means and the above-described air introduction means may be used in combination.

In the seed microorganism cold storage apparatus, so long as the storage of the live seed microorganism in the cold storage can be maintained for a predetermined time (e.g., about several months), it is unnecessary to introduce air into the cold storage to thereby agitate and mix the contents. In such a case, it is unnecessary to provide the above-described agitating means, the above-described air introduction means, etc.

In the automatic feeding apparatus of the present embodiment, the feeding apparatus is provided at the feed opening of the growth tank so as to feed, by means of a pump, the microorganism preparation within the growth tank into oil/fat-including wastewater through the feed pipe. However, the structure of the automatic feeding apparatus is not limited to such a structure so long as the microorganism preparation can be fed to the oil/fat-including wastewater.

For example, the automatic feeding apparatus may be configured such that the growth tank has only a feed opening for the preparation ingredients and does not have a feed opening for the microorganism preparation. In such a case, the feed opening for the preparation ingredients may be used as the feed opening for the microorganism preparation, and a liquid feed means such as a liquid feed pump may be disposed at the feed opening for the preparation ingredients. The microorganism preparation may be fed to the oil/fat-including wastewater through use of the liquid feed means.

INDUSTRIAL APPLICABILITY

The present invention can be used in an industrial field in which wastewater treatment is performed to oil/fat-including wastewater containing a large amount of oil and fat, such as wastewater from a food plant or a grease trap, which is a processing facility of removing, through solid liquid separation, an oil component contained in wastewater from kitchens of the food-service industry. Generation of malodor due to degradation of microorganisms can be prevented, whereby the working environment of workers can be improved. Also, the present invention is industrially useful because the present invention can simplify the step of degrading microorganisms, thereby reducing the number of necessary facilities, and can reduce initial cost of the entire system, maintenance cost, and running cost including electric power consumption, disposal cost of industrial waste, and the like.

DESCRIPTION OF REFERENCE NUMERALS 1 automatic feeding apparatus
11 seed microorganism cold storage apparatus
12 cold storage diffuser
13 activating agent storage
14 carbon source storage
15 water supply apparatus
16 water level monitoring apparatus
17 growth tank diffuser
18 temperature control apparatus
19 feeding apparatus
20 growth tank
21 bottom wall
22 feed opening
23a, 23b sloping surface
30 control section
31 storage control section
32 cleaning control section
33 water storage control section
34 dechlorination control section
35 growth control section
36 feed control section
41 seed microorganism
42 activating agent
43 carbon source
44 oil/fat-including wastewater
50 raw water tank
60 oil and fat decomposing tank
70 active sludge tank
80 precipitation tank
90 sludge storage tank
111 cold storage
112, 123, 131, 141, 173 pipe
113, 132, 142, 192 pump
121, 171 blower
122, 152, 172, 193 valve
124, 174 air discharge opening
125, 175 air discharge portion
151 water source
153 water supply pipe
154 water discharge opening
155 water discharge portion
161 upper level sensor
162 earth sensor
163 lower level sensor
181 thermocouple
191 feed pipe
200 wastewater processing system Accession Numbers

*Yarrowia lipolytica* 1A1 strain NITE BP-1167
*Burkholderia arboris* SL1B1 strain NITE BP-00724
*Candida cylindracea* SL1B2 strain NITE BP-00714

Reference to Deposited Microorganisms

Name of depositary institution: National Institute of Technology and Evaluation (NITE) Patent Microorganisms Depositary
Address of depositary institution: #122, 2-5-8, Kazusakamatari, Kisarazu-shi, Chiba, JAPAN Date of deposit with the institution: Nov. 25, 2011 Accession number given by the institution: NITE BP-1167
Name of depositary institution: National Institute of Technology and Evaluation (NITE) Patent Microorganisms Depositary
Address of depositary institution: #122, 2-5-8, Kazusakamatari, Kisarazu-shi, Chiba, JAPAN
Date of deposit with the institution: Apr. 10, 2018
Accession number given by the institution: NITE BP-00714
The deposited microorganism was converted to international deposit on Apr. 10, 2018, from the microorganism deposited under the national act with National Institute of Technology and Evaluation, NITE Patent Microorganism Depositary on Mar. 6, 2009 (Accession number: NITE P-714).
Name of depositary institution: National Institute of Technology and Evaluation (NITE) Patent Microorganisms Depositary
Address of depositary institution: #122, 2-5-8, Kazusakamatari, Kisarazu-shi, Chiba, JAPAN
Date of deposit with the institution: Apr. 10, 2018
Accession number given by the institution: NITE BP-00724
The deposited microorganism was converted to international deposit on Apr. 10, 2018, from the microorganism deposited under the national act with National Institute of Technology and Evaluation, NITE Patent Microorganism Depositary on Mar. 17, 2009 (Accession number: NITE P-724).

The invention claimed is:

1. A microorganism preparation feeding method characterized by use of a growth tank for growing a seed microorganism belonging to an aerobic microorganism group including at least one species of aerobic microorganisms capable of decomposing oil and fat contained in oil/fat-including wastewater, wherein the seed microorganism belonging to the aerobic microorganism group is maintained in a live state, the seed microorganism is grown in the growth tank by steps of cleaning the growth tank, storing water in the growth tank, and feeding to the growth tank the seed microorganism, so as to produce a microorganism preparation, and the produced microorganism preparation is fed to the oil/fat-including wastewater, the method comprising: feeding to the growth tank, as a source material, the seed microorganism which is maintained in the live state by means of a cold storage apparatus being controlled so that the temperature is 0° C. to 20° C. and whose population density is $1 \times 10^7$ CFU/mL to $5 \times 10^9$ CFU/mL in the cold storage apparatus; growing the seed microorganism in a seed volume by means of the growth tank so as to produce the microorganism preparation whose volume is 50 to 500 times the seed volume of the seed microorganism and whose population density is $1 \times 10^7$ CFU/mL to $2 \times 10^{10}$ CFU/mL; and feeding the produced microorganism preparation to the oil/fat-including wastewater; wherein the seed microorganism is maintained in the live state by introducing air into the seed microorganism of the cold storage apparatus and generating convection for agitating and mixing the seed microorganism.

2. The microorganism preparation feeding method according to claim 1, wherein the growth of the seed microorganism in the growth tank is performed by use of the seed microorganism in the seed volume, water, an activating agent for activating the seed microorganism, and a carbon source composed of vegetable oil and growing the seed microorganism; and introducing air into the seed microorganism and generating convection for agitating and mixing the seed microorganism.

3. The microorganism preparation feeding method according to claim 2, wherein the activating agent contains nitrogen, phosphorus, and potassium.

4. The microorganism preparation feeding method according to claim 1, wherein the growth of the seed microorganism is repeatedly performed every day such that the seed microorganism is grown once every 24 hours.

5. The microorganism preparation feeding method according to claim 1, wherein the method comprises: a cleaning step of cleaning the growth tank at a first timing; a water storage step of storing water of a predetermined amount in the growth tank at a second timing; a growing step of supplying at a third timing to the growth tank the seed microorganism in the seed volume, an activating agent for activating the seed microorganism, and a carbon source composed of vegetable oil and growing the seed microorganism in respective predetermined amounts, and growing the seed microorganism to have a population density in a predetermined range by introducing air into a resultant mixture simultaneously with agitating and mixing the resultant mixture in a state in which the resultant mixture is maintained at a constant temperature; and a feeding step of feeding the microorganism preparation produced in the growing step to the oil/fat-including wastewater in a predetermined amount at a fourth timing.

6. The microorganism preparation feeding method according to claim 5, wherein the cleaning step, the water storage step, the growing step, and the feeding step are repeatedly performed every day such that each of the steps is performed once every 24 hours.

7. The microorganism preparation feeding method according to claim 5, wherein each of the cleaning step, the water storage step, the growing step, and the feeding step is repeatedly performed at intervals of 48 hours in each of two growth tanks such that each step is performed once every 48 hours and a time shift of 24 hours is present between each of the steps performed in one growth tank and a corresponding one of the steps performed in the other growth tank, whereby the microorganism preparation is fed to the oil/fat-including wastewater from the two growth tanks every day.

8. The microorganism preparation feeding method according to claim 5, further comprising a dechlorination step of performing aeration for a predetermined period of time after tap water has been supplied to and stored in the growth tank, thereby removing chlorine from the tap water.

9. The microorganism preparation feeding method according to claim 1, wherein the growth tank is a tubular growth tank whose entirety is elongated in the vertical direction, and comprises a diffuser which has a plurality of air discharge openings provided at an end of an air discharge portion located at a lower region of the growth tank so as to introduce air into contents of the growth tank and generate convection for agitating and mixing the microorganism preparation.

10. The microorganism preparation feeding method according to claim 1, wherein the aerobic microorganism group includes *Yarrowia lipolytica* 1A1 strain NITE BP-1167.

11. The microorganism preparation feeding method according to claim 1, wherein the aerobic microorganism group includes *Burkholderia arboris* SL1B1 strain NITE BP-00724.

\* \* \* \* \*